United States Patent
Rowe

(10) Patent No.: US 12,044,671 B2
(45) Date of Patent: Jul. 23, 2024

(54) GAS DETECTION INTEGRATION INTO A GAS EXTRACTOR

(71) Applicant: Halliburton Energy Services, Inc., Houston, TX (US)

(72) Inventor: Mathew Dennis Rowe, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 285 days.

(21) Appl. No.: 17/578,978

(22) Filed: Jan. 19, 2022

(65) Prior Publication Data

US 2023/0003709 A1    Jan. 5, 2023

Related U.S. Application Data

(63) Continuation of application No. PCT/US2021/039949, filed on Jun. 30, 2021.

(51) Int. Cl.
*G01N 33/28* (2006.01)
*E21B 49/08* (2006.01)

(52) U.S. Cl.
CPC ..... *G01N 33/2841* (2013.01); *E21B 49/0875* (2020.05); *G01N 2201/0686* (2013.01)

(58) Field of Classification Search
CPC ............ E21B 49/0875; G01N 33/2841; G01N 2201/0686
See application file for complete search history.

(56) References Cited

U.S. PATENT DOCUMENTS

| | | | | |
|---|---|---|---|---|
| 2,514,690 A | * | 7/1950 | Bliss ...................... | G01N 27/16 73/19.09 |
| 2,704,658 A | * | 3/1955 | Gordon .................... | B01F 27/91 175/206 |
| 2,792,072 A | * | 5/1957 | Moore ................... | E21B 49/005 96/217 |
| 4,507,558 A | * | 3/1985 | Bonne ................... | G01N 21/031 250/343 |
| 5,090,256 A | * | 2/1992 | Issenmann ......... | G01N 33/2823 73/863.23 |

(Continued)

FOREIGN PATENT DOCUMENTS

| CN | 207650099 | 7/2018 |
|---|---|---|
| JP | 2017-129485 | 7/2017 |

OTHER PUBLICATIONS

International Search Report and Written Opinion for Application No. PCT/US2021/039949, dated Mar. 21, 2022.

*Primary Examiner* — John Fitzgerald
(74) *Attorney, Agent, or Firm* — Benjamin Ford; C. Tumey Law Group PLLC

(57) ABSTRACT

The present disclosure generally relates to a standalone gas extraction and detection system comprising a gas extraction chamber operable to receive a wellbore fluid and a carrier gas; a gas detection chamber in fluid communication with the gas extraction chamber, the gas detection chamber comprising reflective surfaces operable to receive infrared radiation (IR) and an extracted gas sample from the gas extraction chamber; an open-path detector operable to detect the IR in the gas detection chamber; and a shaft extending through the gas extraction chamber and the gas detection chamber of the standalone gas extraction and detection system.

19 Claims, 5 Drawing Sheets

(56) References Cited

U.S. PATENT DOCUMENTS

| | | | | |
|---|---|---|---|---|
| 5,163,332 | A * | 11/1992 | Wong | G01N 21/0303 250/338.5 |
| 5,170,064 | A * | 12/1992 | Howe | G01N 21/3504 250/573 |
| 5,199,509 | A * | 4/1993 | Wright | E21B 49/005 175/206 |
| 5,222,389 | A * | 6/1993 | Wong | G08B 17/117 250/338.5 |
| 5,648,603 | A * | 7/1997 | Hanson | B01D 19/0057 73/863 |
| 7,616,316 | B1 * | 11/2009 | Silver | G01N 21/3504 356/409 |
| 7,710,568 | B1 * | 5/2010 | Paige | G01J 3/0272 356/73 |
| 7,779,667 | B2 * | 8/2010 | Evrard | E21B 49/005 73/19.09 |
| 8,632,625 | B2 * | 1/2014 | DeGreeve | E21B 49/005 96/204 |
| 9,528,335 | B2 * | 12/2016 | Henderson | B01D 19/0094 |
| 9,651,481 | B2 * | 5/2017 | DeGreeve | E21B 21/067 |
| 9,671,332 | B2 * | 6/2017 | Christensen | G01N 21/3504 |
| 10,001,465 | B2 | 6/2018 | Mitchell | |
| 10,180,396 | B2 * | 1/2019 | DeGreeve | G01V 8/10 |
| 10,247,665 | B2 * | 4/2019 | Rissing | G01N 21/031 |
| 10,704,347 | B2 * | 7/2020 | Bentamy | G01N 33/0011 |
| 10,808,528 | B2 * | 10/2020 | Rowe | E21B 21/01 |
| 11,480,053 | B2 * | 10/2022 | Rowe | E21B 49/084 |
| 11,566,519 | B2 * | 1/2023 | Al-Qasim | E21B 21/002 |
| 2003/0147080 | A1 * | 8/2003 | Sarkis | G01N 21/359 356/437 |
| 2004/0265176 | A1 * | 12/2004 | Kerherve | G01N 33/2823 422/68.1 |
| 2006/0254421 | A1 * | 11/2006 | Boone | E21B 21/067 95/260 |
| 2008/0277586 | A1 * | 11/2008 | Cardinale | G01N 21/3504 250/339.13 |
| 2013/0263647 | A1 | 10/2013 | Barrett et al. | |
| 2014/0204382 | A1 * | 7/2014 | Christensen | G01N 21/3504 356/402 |
| 2014/0268157 | A1 * | 9/2014 | Bogoev | G01N 21/15 356/437 |
| 2018/0156034 | A1 | 6/2018 | Mitchell et al. | |
| 2018/0245466 | A1 | 8/2018 | Gosney et al. | |
| 2019/0135950 | A1 * | 5/2019 | Gonioukh | C08F 210/02 |
| 2019/0368345 | A1 | 12/2019 | Rowe et al. | |
| 2019/0390524 | A1 | 12/2019 | Bentamy et al. | |
| 2020/0215460 | A1 | 7/2020 | Henderson et al. | |
| 2020/0256188 | A1 | 8/2020 | Rowe | |
| 2021/0389239 | A1 | 12/2021 | Rowe | |
| 2021/0404273 | A1 | 12/2021 | Rowe | |

* cited by examiner

GAS DETECTION INTEGRATION INTO A GAS EXTRACTOR

BACKGROUND

During wellbore operations, such as, for example, drilling through a subterranean formation, various fluids may move through a wellbore and to the surface. The fluid may be analyzed at the surface to characterize the depositional environment and optimize drilling therethrough. For example, the fluid analysis may allow an operator to identify and quantify fluids such as oil, gas, water, and/or other formation fluids at various depths within the subterranean formation.

Typical surface equipment to perform this analysis, such as a gas detector and a gas extractor, may each be positioned at separate surface locations, requiring a substantial amount of space at a rig site with a limited amount of space. Further, this separation between the gas detector and the gas extractor may require additional time, cost, and/or space to rig up additional gas lines to connect the gas extractor to the gas detector. Further, gas samples may become contaminated with moisture while passing through the gas lines from the gas extractor to the gas detector.

BRIEF DESCRIPTION OF THE DRAWINGS

These drawings illustrate certain aspects of some examples of the present disclosure and should not be used to limit or define the disclosure.

DETAILED DESCRIPTION

Figure 1:
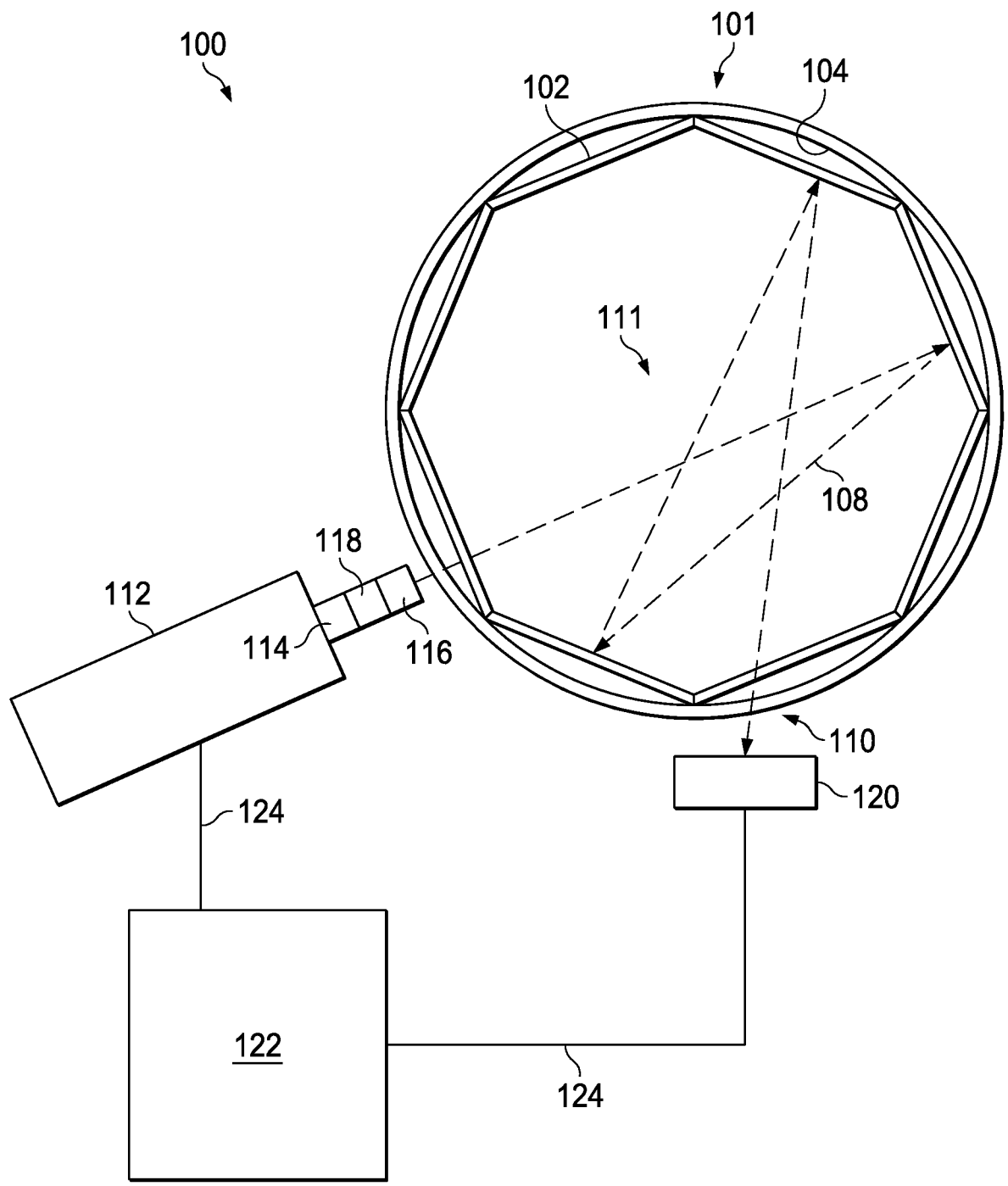
FIG. 1 illustrates an open-path laser detection device (OPDD), in accordance with examples of the present disclosure.

The present disclosure generally relates to gas extractors, and, more particularly, examples relate to systems and methods for integrating a gas detector into a gas extractor and using open-path laser detection to provide a standalone gas analysis unit for deployment to a rig site. In particular examples, an open-path laser detection device (OPDD) may include a gas detection chamber mounted onto or integrated into a gas extraction chamber. The OPDD may employ spectroscopy to determine a type and quantity of at least one component/molecular species within a wellbore fluid. For example, the OPD may utilize deuterated triglycine sulfate (DTGS), mercury cadmium telluride (MCT), or other suitable methods, to provide molecular species detection or total hydrocarbon detection in a drilling fluid.

In some examples, the OPDD may operate similar to Fourier-Transform Infrared (FTIR) spectroscopy, chirped laser dispersion spectroscopy, tunable diode laser (TDL) spectroscopy or other spectroscopy that may function on an open path. The OPDD may replace total gas detection, gas chromatography, or other gas detection methods.

For example, the gas detection chamber may be coupled to an infrared (IR) energy source, such as, a laser. The laser may utilize a single wavelength, a tunable diode, or quantum cascading to emit radiation. In some examples, the laser may include a monochromatic filter, an adjustable mirror to control wavelength, and/or a reference cell filled with a desired gas for laser calibration. A detector may also be coupled to the gas detection chamber and may detect and convert the energy emitted from the energy source within the gas detection chamber, into measurable signals. Based on the signals, the type and quantity of at least one component/molecular species within the wellbore fluid may be determined.

In some examples, a set of reflective surfaces may be mounted in the gas detection chamber. The reflective surfaces may be flat or curved to reflect/bounce a laser beam between the surfaces to maximize a free path length (i.e., a maximum traveled distance by the laser beam).

Additionally, the gas detection chamber may be vibrationally isolated from adjacent structures/supports via active or passive vibration dampening/canceling systems. An active vibration isolation system may include a sensor, an actuator, and a controller to produce an opposing vibration to cancel/counteract an incoming vibration; whereas, the passive vibration isolation system may include dampeners, rubber, springs, airbags, and/or other mechanical structure(s) that are not actively operated.

In some examples, a shaft may pass through the gas detection chamber to rotate a gas extraction device within the gas extraction chamber. The gas extraction device may include, for example, a rotor to facilitate the gas extraction via rotation. The shaft may pass through a soft connector (e.g., a hose) or a hard connector (e.g., a pipe).

In some examples, a carrier gas may pass into the gas extraction chamber to carry extracted gas from drilling fluid into the gas detection chamber. In other examples, a mixing chamber may be utilized to receive and mix the carrier gas and the extracted gas, for passage into the gas detection chamber.

FIG. 1 illustrates an OPDD 100, in accordance with examples of the present disclosure. The OPDD 100 may include a detection chamber 101 to receive a desired gas for analysis. The gas may be acquired during wellbore operations, such as drilling for example. The detection chamber 101 may include a set of reflective surfaces 102 (e.g., mirrors), which may be disposed along a perimeter 104 within the detection chamber 101, for example. In non-limiting examples, the reflective surfaces 102 may form a polygon within a circular detection chamber 101. The reflective surfaces 102 may be flat or curved and may be disposed along the perimeter 104 (e.g., a wall) to reflect/bounce a laser beam 108 between the reflective surfaces 102 to maximize a free path length (i.e., a maximum traveled distance by the laser beam 108 within the detection chamber 101).

The laser beam 108 may pass through an exit 110 from the detection chamber 101 after moving along the free path length. In some examples, an obstruction, such as, for example, a shaft (e.g., shown on FIG. 2) may pass through the detection chamber 101 (e.g., a center passage 111 of the detection chamber 101) to actuate or rotate a gas extraction device within a gas extraction chamber (e.g., shown on FIG. 2). The laser beam 108 may include a travel path that avoids any obstruction(s) within the gas detection chamber 101.

An energy source 112, such as, for example, a laser may be coupled (e.g., weld, fasteners) to the detection chamber 101. The energy source 112 may utilize a single wavelength, a tunable diode, or quantum cascading. In some examples, the energy source 112 may include a monochromatic filter 114, an adjustable mirror 116 to control wavelength, and/or a reference cell 118 filled with a desired gas for calibration of the energy source 112 (e.g., laser calibration).

A detector 120 (e.g., a radiation transducer, a photon detector) may also be coupled to the detection chamber 101 and may convert radiation (e.g., photons) within the detection chamber 101 into measurable signals (e.g., electrical signals). The detector 120 may be disposed adjacent to the exit 110 of the detection chamber 101 to receive the laser beam 108. In some examples, the detector 120 may be an open laser path detector rather than a single laser point detector. For example, the sample gas may intersect a laser beam before contacting a single laser point. Open-path detectors may also be cost-effective in scenarios where a row of point detectors might be implemented to achieve the same coverage/detection area.

The energy source 112 and the detector 120 may be in communication with a system controller 122 via communication paths 124 (e.g., wires or wireless). The system controller 122 may include a display, a storage unit, and/or any instrumentality or aggregate of instrumentalities operable to compute, estimate, classify, process, transmit, receive, retrieve, originate, switch, store, display, manifest, detect, record, reproduce, handle, or utilize any form of information, intelligence, or data for business, scientific, control, or other purposes. For example, the system controller 122 may be a computer, a network storage device, or any other suitable device and may vary in size, shape, performance, functionality, and price. The system controller 122 may include a processing unit (e.g., microprocessor, central processing unit, programmable logic controller (PLC), etc.) that may process data by executing software or instructions obtained from a local non-transitory computer readable media (e.g., optical disks, magnetic disks). The non-transitory computer readable media may store software or instructions of the methods described herein. Non-transitory computer readable media may include any instrumentality or aggregation of instrumentalities that may retain data and/or instructions for a period of time. The non-transitory computer readable media may include, for example, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; as well as communications media such wires, optical fibers, microwaves, radio waves, and other electromagnetic and/or optical carriers; and/or any combination of the foregoing.

The system controller 122 may also include input device(s) (e.g., keyboard, mouse, touchpad, etc.) and output device(s) (e.g., monitor, printer, etc.). The input device(s) and output device(s) provide a user interface. For example, the system controller 122 may enable an operator to select and perform analysis, view collected data, view analysis results, and/or perform other tasks.

Figure 2:
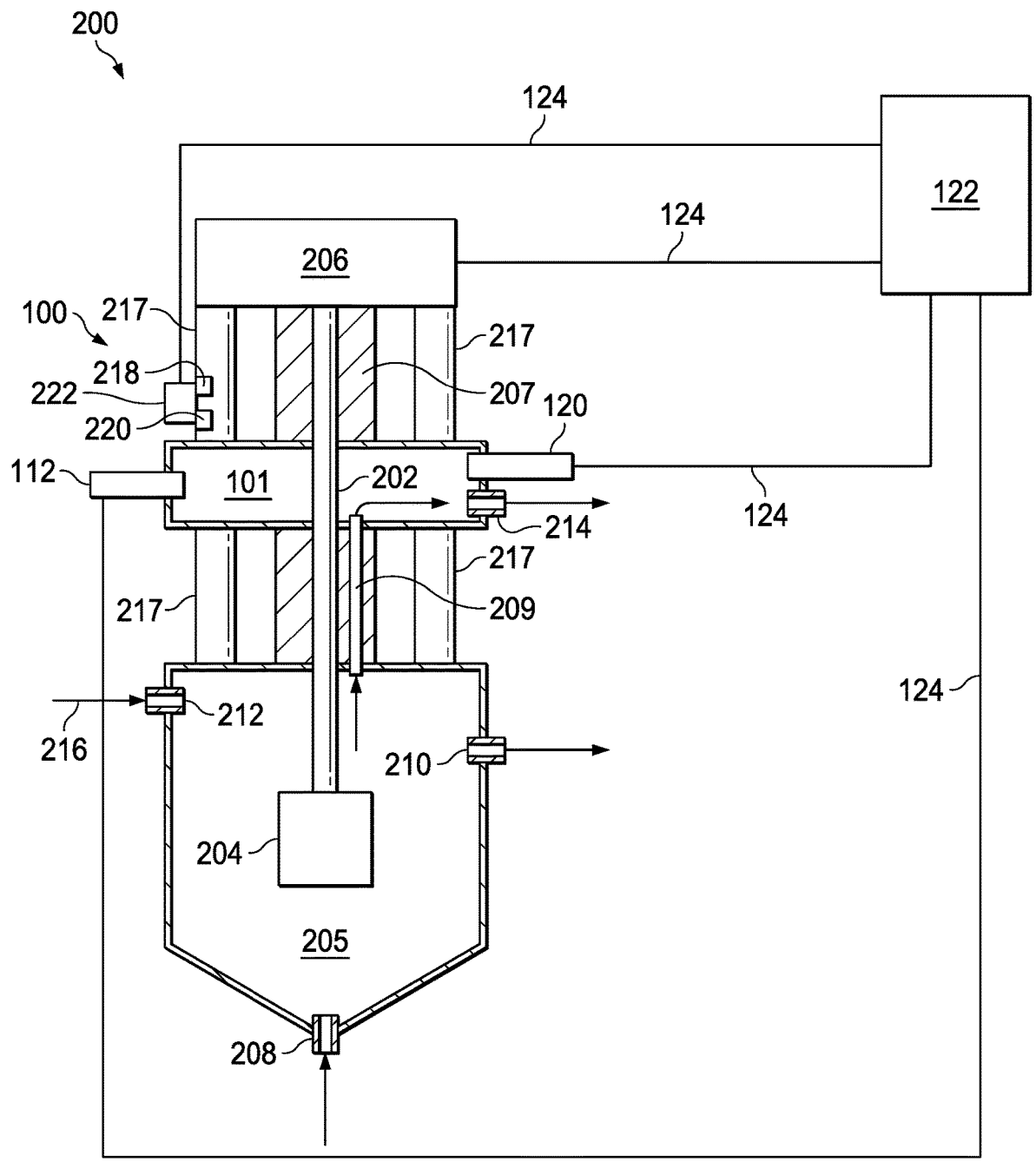
FIG. 2 illustrates a standalone integrated gas extraction and detection system including the OPDD, in accordance with examples of the present disclosure.

FIG. 2 illustrates a system 200 including the OPDD 100, in accordance with examples of the present disclosure. The OPDD 100 may be vertically integrated into the system 200 (e.g., a standalone gas analysis unit in a stacked configuration). As noted previously, a shaft 202 may pass through the OPDD 100 via the detection chamber 101 to actuate or rotate a gas extraction device 204 (e.g., a rotor) within a gas extraction chamber 205 via a motor 206. In some examples, the gas extraction device 204 may be operable to extract gases from the sample fluid based on a density and/or a viscosity differential between the various fluid components of the sample fluid.

The shaft 202 may be disposed within a sleeve 207 (e.g., a soft connector, flexible hose) that may also include a conduit 209 fluidly coupling the detection chamber 101 to the extraction chamber 205. In some examples, the soft connector may be employed because alignment of the mirrors and electromagnetic source to the detector may be affected by vibration. Additionally, vibration may add noise to the signal.

The gas extraction chamber 205 may include an inlet 208 (e.g., a valve) and an outlet 210 (e.g., a valve) to pass a wellbore fluid therethrough. Non-limiting examples of the wellbore fluid may include a drilling fluid, a production fluid, a completion fluid, a fracking fluid, a wellbore treatment fluid, a reservoir fluid, a gas, oil, or water. For example, the system 200 may be implemented into a rig site such a drilling rig or production platform. In some examples, the system 200 may implemented at the possum belly, the mud tanks, and/or a header box associated with a fluid processing unit (e.g., a shale shaker).

The gas extraction chamber 205 may also include an inlet 212 (e.g., a valve) for ingress of a carrier gas to transport at least one extracted gas from the wellbore fluid in the gas extraction chamber 205 to the detection chamber 101 via the conduit 209 to receive emitted energy from the energy source 112 for detection by the detector 120. The carrier gas may be an inert gas including, but not limited to, nitrogen, helium, neon, or argon. In some examples, the carrier gas may be an atmospheric gas, a non-atmospheric gas, or a gas with a sufficient oxygen content to allow for increased sensitivity and reduced contamination from helium, water, or sulfur, for example.

The chamber 101 may include an outlet 214 to remove gases from the chamber 101 after detection via the detector 120 (e.g., an open path detector). The flow of the fluids through the system 200 is depicted with directional arrows 216. Additionally, the chamber 101 may be vibrationally isolated from adjacent structures/supports via dampeners 217. The dampeners 217 may include active and/or passive vibration dampening/canceling systems. An active vibration isolation system may include a sensor 218, an actuator 220, and a controller 222 to produce an opposing vibration to cancel/counteract an incoming vibration. In contrast to the active vibration isolation system, the passive vibration isolation system may include dampeners, rubber, springs, airbags, and/or other mechanical structure(s). The system controller 122 may operate the system 200 via at least the communication paths 124, for example.

Figure 3:
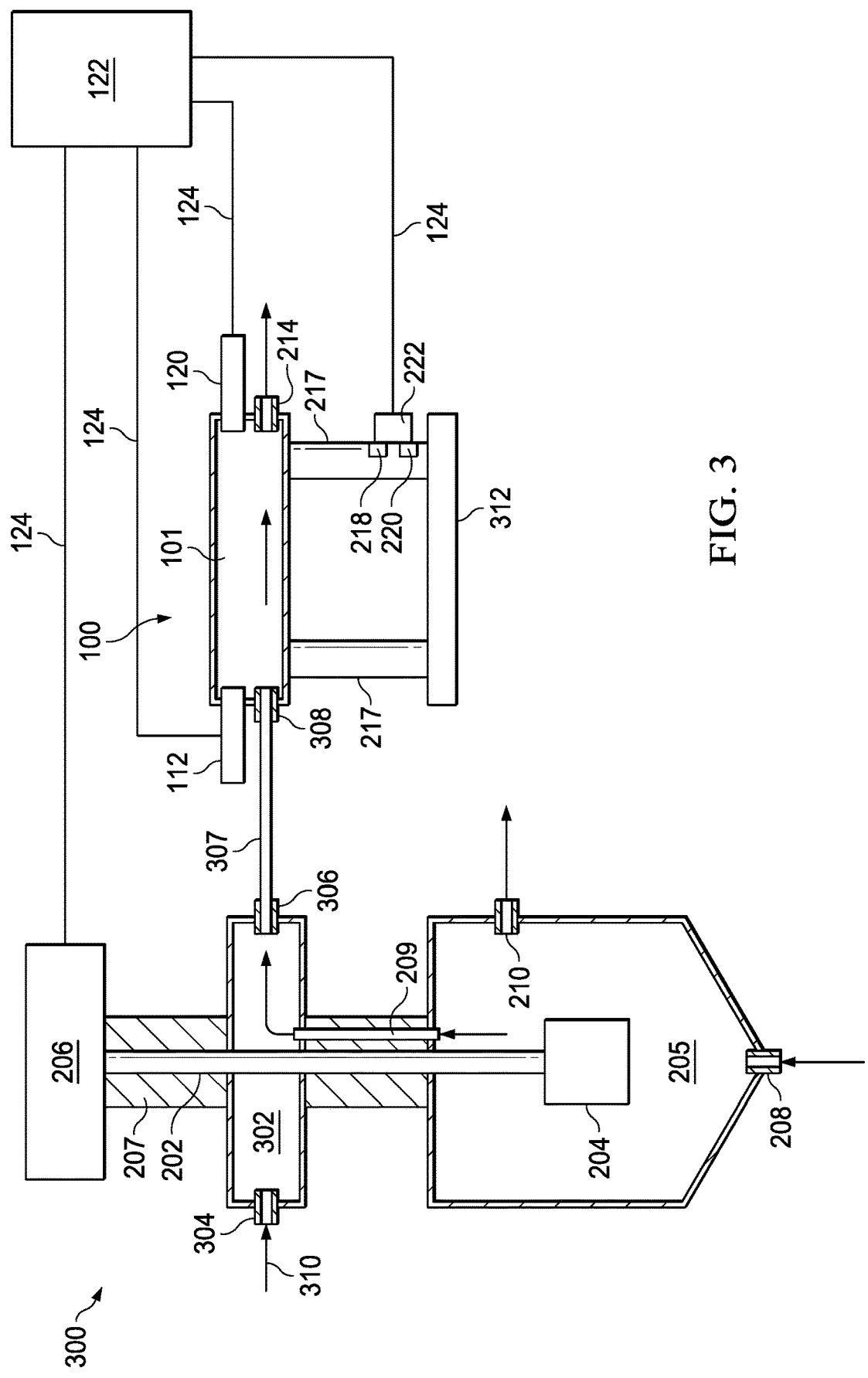
FIG. 3 illustrates another standalone integrated gas extraction and detection system including the OPDD and a mixing chamber, in accordance with examples of the present disclosure.

FIG. 3 illustrates a system 300 including the OPDD 100 in an alternate configuration, in accordance with examples of the present disclosure. In contrast to the stacked configuration of the system 200 of FIG. 2, the OPDD 100 may be integrated into the system 300 horizontally, rather than vertically. For example, the OPDD 100 may be disposed on a lateral side(s) of other components, such that a flow of sample gas passes laterally into the detection chamber 101 rather than pass vertically from the extraction chamber 205, as shown in the system 200 of FIG. 2. The system 300 may also provide a standalone gas analysis unit similar to the system 200.

Further, the system 300 includes a mixing chamber 302 which may be in fluid communication with the gas extraction chamber 205 via the conduit 209. The shaft 202 may pass through the mixing chamber 302 to actuate or rotate a gas extraction device 204 (e.g., a rotor) within the gas extraction chamber 205 via the motor 206. The shaft 202 may be disposed within the sleeve 207 (e.g., a hard connector, rigid pipe) that may also include the conduit 209 which may fluidly couple the chamber 205 with the mixing chamber 302. In some examples, a hard connector may be employed due to ease of handling.

The mixing chamber 302 may include an inlet 304 and an outlet 306 to allow carrier and sample/extracted gases to pass therethrough and into the detection chamber 101 via a conduit 307 and an inlet 308 (e.g., a valve). In the detection chamber 101, the extracted gas may receive emitted energy from the energy source 112 for detection by the detector 120. The flow of the fluids through the system 300 is depicted with directional arrows 310. Additionally, the chamber 101 may be vibrationally isolated from adjacent structures/supports (e.g., a fixed support 312) via the dampeners 217. The active vibration isolation system may include the sensor 218, the actuator 220, and the controller 222 to produce the opposing vibration to cancel/counteract the incoming vibration. In contrast to the active vibration isolation system, the passive vibration isolation system may include dampeners, rubber, springs, airbags, and/or other mechanical structure(s), as noted previously. The system controller 122 may operate the system 300 via at least the communication paths 124, for example.

Figure 4:
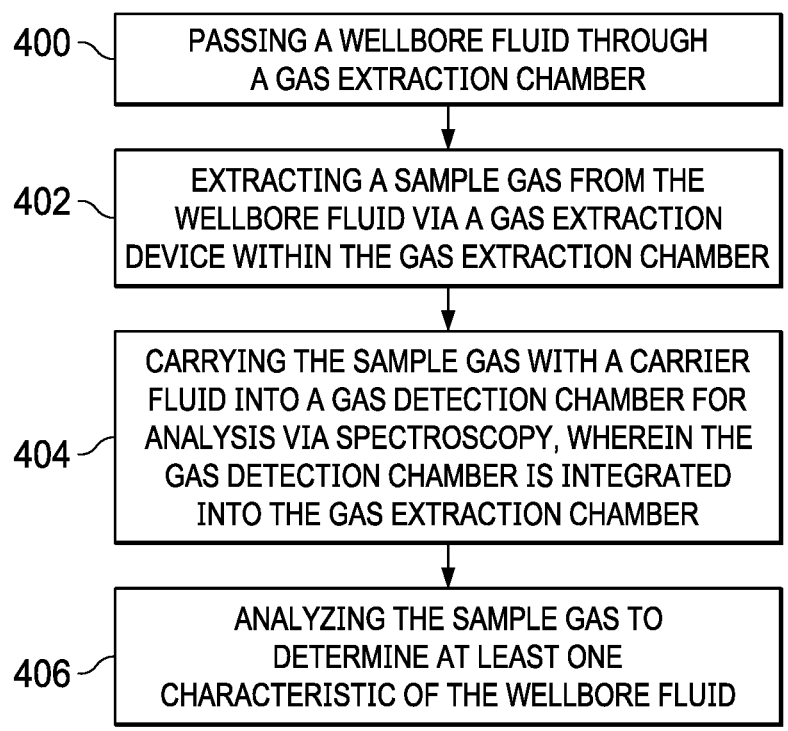
FIG. 4 illustrates an operative flow sequence for the standalone integrated gas extraction and detection systems, in accordance with examples of the present disclosure.

FIG. 4 illustrates an exemplary flow diagram of an integrated gas extraction and detection technique, in accordance with examples of the present disclosure. At step 400, a wellbore fluid may pass through the gas extraction chamber 205 (e.g., shown on FIGS. 2 and 3). At step 402, a sample gas may be extracted from the gas extraction chamber 205 due to rotation of the gas extraction device 204 within the gas extraction chamber 205. The gas may be extracted into the detection chamber 101 (e.g., shown on FIGS. 2 and 3) for analysis.

At step 404, a carrier gas may facilitate movement of the sample gas into the detection chamber for analysis via spectroscopy, wherein the gas detection chamber is integrated into the gas extraction chamber. In some examples, the mixing chamber 302 (e.g., shown on FIG. 3) may be implemented to mix the carrier gas with an extracted gas. At step 406, the system controller 122 may determine at least one characteristic of the wellbore fluid based on analysis of the sample gas.

Figure 5:
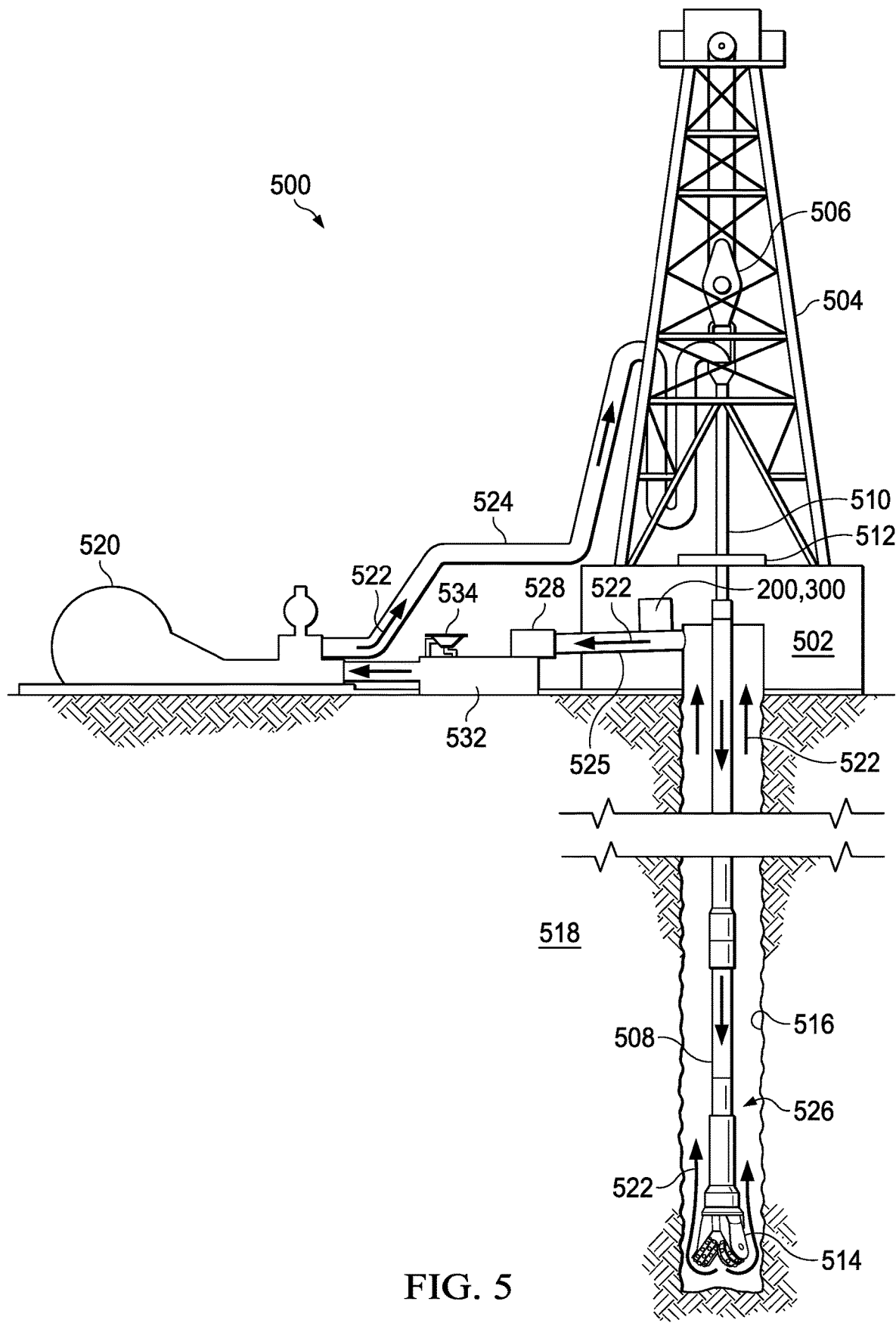
FIG. 5 illustrates a standalone integrated gas extraction and detection system implemented at a rig site, in accordance with examples of the present disclosure.

FIG. 5 illustrates the system 200 or the system 300 implemented at a rig site 500, in accordance with examples of the present disclosure. The rig site 500 may include a drilling platform 502 that supports a derrick 504 having a traveling block 506 for raising and lowering a drill string 508. A kelly 510 (or top drive) suspends the drill string 508 as it passes through a rotary table 512. A drill bit 514 is attached to the distal end of the drill string 508 and is driven either by a downhole motor and/or via rotation of the drill string 508 from the well surface. The drill bit 514 may rotate to create a wellbore 516 that extends into a subterranean formation 518. It should be noted that although FIG. 1 illustrates a land-based drilling rig, the principles described herein also apply to subsea drilling operations that may employ floating or sea-based platforms and rigs.

A pump 520 (e.g., a mud pump) circulates a fluid 522 (e.g., a drilling fluid, wellbore fluid) through a feed pipe 524 and into the drill string 508. The fluid 122 may be conveyed through the drill string 508 and the drill bit 514 and out into the wellbore 116. The fluid 522 is then circulated back to the surface via an annulus 526 defined between the drill string 508 and the walls of the wellbore 516. At the surface, the circulated fluid 522 exits the annulus 526 and may be conveyed, continuously or periodically, to the system 200 or the system 300, for spectral analysis before being returned back into the circulatory system. In some examples, the system 200 or the system 300 may be disposed at a flow line 525. In other examples, the system 200 or the system 300 may be placed at another suitable location within the circulatory system such as at the possum belly, the mud tanks, and/or a header box associated with a fluid processing unit 528 (e.g., shale shaker). The system 200 or the system 300 may employ spectroscopy via open path detection, as previously described, to determine a type and quantity of at least one component/molecular species within the fluid 522. For example, the system 200 or the system 300 may utilize deuterated triglycine sulfate (DTGS), mercury cadmium telluride (MCT), or other suitable methods, to provide molecular species detection or total hydrocarbon.

After passing the system 200 or the system 300, the circulated fluid 522 may pass into the fluid processing unit 528. After passing through the fluid processing unit 528, a "clean" fluid 522 is deposited into a mud pit 532. One or more chemicals, fluids, or additives may be added to the fluid 522 via a mixing hopper 534.

Once the chemical composition of the fluid is determined, the data may be used by an analyst, mud logger, geochemist, geologist, petrophysicist, or other well to identify, for example, a hydrocarbon-bearing zone. Additionally, the data may be used to alter drilling parameters or a drilling fluid composition.

Accordingly, the systems and methods of the present disclosure may allow for open-path spectral analysis of an extracted gas by integrating a gas detector into a gas extractor. The configurations as described herein may provide for robust standalone integrated gas extraction and detection units to facilitate deployment and installation at rig sites. The systems and methods may include any of the various features disclosed herein, including one or more of the following statements.

Statement 1. A standalone gas extraction and detection system comprises a gas extraction chamber operable to receive a wellbore fluid and a carrier gas; a gas detection chamber in fluid communication with the gas extraction chamber, the gas detection chamber comprising reflective surfaces operable to receive infrared radiation (IR) and an extracted gas sample from the gas extraction chamber; an open-path detector operable to detect the IR in the gas detection chamber; and a shaft extending through the gas extraction chamber and the gas detection chamber of the standalone gas extraction and detection system.

Statement 2. The standalone gas extraction and detection system of the statement 1, wherein the shaft is coupled to a gas extraction device.

Statement 3. The standalone gas extraction and detection system of the statement 1 or the statement 2, wherein the gas extraction device comprises a rotor.

Statement 4. The standalone gas extraction and detection system of any one of the preceding statements, further comprising a motor operable to rotate the shaft.

Statement 5. The standalone gas extraction and detection system of any one of the preceding statements, further comprising dampeners to vibrationally isolate the gas detection chamber from other components of the standalone gas extraction and detection system.

Statement 6. The standalone gas extraction and detection system of any one of the preceding statements, wherein the dampeners are active dampeners.

Statement 7. The standalone gas extraction and detection system of any one of the preceding statements, wherein the dampeners are passive.

Statement 8. The standalone gas extraction and detection system of any one of the preceding statements, wherein the gas detection chamber is operable to receive a sample gas from a conduit extending vertically from the gas extraction chamber.

Statement 9. A standalone gas extraction and detection system comprising: a gas extraction chamber operable to receive a wellbore fluid; a mixing chamber in fluid communication with the gas extraction chamber, the mixing chamber in fluid communication with the gas extraction chamber, the mixing chamber operable to receive a carrier gas and an extracted gas sample from the wellbore fluid; a gas detection chamber in fluid communication with the mixing chamber, the gas detection chamber comprising reflective surfaces operable to receive infrared radiation (IR); an open-path detector operable to detect the IR in the gas detection chamber; and a shaft extending through the gas extraction chamber and the mixing chamber of the standalone gas extraction and detection system.

Statement 10. The standalone gas extraction and detection system of the statement 9, further comprising a conduit extending vertically to fluidly couple the gas extraction chamber with the mixing chamber.

Statement 11. The standalone gas extraction and detection system of the statement 9 or 10, further comprising a conduit extending horizontally to fluidly couple the mixing chamber with the gas detection chamber.

Statement 12. The standalone gas extraction and detection system of any one of the statements 9-11, further comprising a motor operable to rotate the shaft.

Statement 13. The standalone gas extraction and detection system of any one of the statements 9-12, further comprising further comprising dampeners to vibrationally isolate the gas detection chamber from other components of the standalone gas extraction and detection system.

Statement 14. The standalone gas extraction and detection system of any one of the statements 9-13, wherein the dampeners are active dampeners.

Statement 15. The standalone gas extraction and detection system of any one of the statements 9-14, wherein the dampeners are passive dampeners.

Statement 16. A method for extracting and detecting a gas, the method comprising: extracting the gas from a wellbore fluid that is disposed within an extraction chamber of a standalone gas extraction and detection system; allowing extracted gas to move into a detection chamber that is integrated into the extraction chamber of the standalone gas extraction and detection system; and detecting infrared radiation via an open-path detector to analyze the extracted gas that is disposed within the detection chamber.

Statement 17. The method of the statement 16, further comprising moving a shaft that extends through the extraction chamber and the detection chamber to extract the gas from the wellbore fluid.

Statement 18. The method of the statement 16 or 17, further comprising mixing the extracted gas with a carrier fluid for passage into the detection chamber.

Statement 19. The method of any one of the statements 16-18, further comprising vibrationally isolating the gas detection chamber from other components of the standalone gas extraction and detection system with active dampeners.

Statement 20. The method of any one of the statements 16-19, further comprising vibrationally isolating the gas detection chamber from other components of the standalone gas extraction and detection system with passive dampeners.

Although the present disclosure and its advantages have been described in detail, it should be understood that various changes, substitutions and alterations may be made herein without departing from the spirit and scope of the disclosure as defined by the appended claims. The preceding description provides various examples of the systems and methods of use disclosed herein which may contain different method steps and alternative combinations of components. It should be understood that although individual examples may be discussed herein, the present disclosure covers all combinations of the disclosed examples, including, without limitation, the different component combinations, method step combinations, and properties of the system. It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the elements that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present examples are well adapted to attain the ends and advantages mentioned as well as those that are inherent therein. The particular examples disclosed above are illustrative only and may be modified and practiced in different but equivalent manners apparent to those skilled in the art having the benefit of the teachings herein. Although individual examples are discussed, the disclosure covers all combinations of all of the examples. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative examples disclosed above may be altered or modified and all such variations are considered within the scope and spirit of those examples. If there is any conflict in the usages of a word or term in this specification and one or more patent(s) or other documents that may be incorporated herein by reference, the definitions that are consistent with this specification should be adopted.

What is claimed is:

1. A standalone gas extraction and detection system comprising:
    a gas extraction chamber operable to receive a wellbore fluid and a carrier gas;
    a gas detection chamber in fluid communication with the gas extraction chamber, the gas detection chamber comprising reflective surfaces operable to receive infrared radiation (IR) and an extracted gas sample from the gas extraction chamber;
    an open-path detector operable to detect the IR in the gas detection chamber; and
    a shaft extending through the gas extraction chamber and the gas detection chamber of the standalone gas extraction and detection system.

2. The standalone gas extraction and detection system of claim 1, further comprising a motor operable to rotate the shaft.

3. The standalone gas extraction and detection system of claim 1, wherein the gas detection chamber is operable to receive a sample gas from a conduit extending vertically from the gas extraction chamber.

4. The standalone gas extraction and detection system of claim 1, wherein the shaft is coupled to a gas extraction device.

5. The standalone gas extraction and detection system of claim 4, wherein the gas extraction device comprises a rotor.

6. The standalone gas extraction and detection system of claim 1, further comprising dampeners to vibrationally isolate the gas detection chamber from other components of the standalone gas extraction and detection system.

7. The standalone gas extraction and detection system of claim 6, wherein the dampeners are active dampeners.

8. The standalone gas extraction and detection system of claim 6, wherein the dampeners are passive dampeners.

9. A standalone gas extraction and detection system comprising:
    a gas extraction chamber operable to receive a wellbore fluid;
    a mixing chamber in fluid communication with the gas extraction chamber, the mixing chamber in fluid communication with the gas extraction chamber, the mixing chamber operable to receive a carrier gas and an extracted gas sample from the wellbore fluid;
    a gas detection chamber in fluid communication with the mixing chamber, the gas detection chamber comprising reflective surfaces operable to receive infrared radiation (IR);
    an open-path detector operable to detect the IR in the gas detection chamber; and
    a shaft extending through the gas extraction chamber and the mixing chamber of the standalone gas extraction and detection system.

10. The standalone gas extraction and detection system of claim 9, further comprising a conduit extending vertically to fluidly couple the gas extraction chamber with the mixing chamber.

11. The standalone gas extraction and detection system of claim 9, further comprising a conduit extending horizontally to fluidly couple the mixing chamber with the gas detection chamber.

12. The standalone gas extraction and detection system of claim 9, further comprising a motor operable to rotate the shaft.

13. The standalone gas extraction and detection system of claim 9, further comprising dampeners to vibrationally isolate the gas detection chamber from other components of the standalone gas extraction and detection system.

14. The standalone gas extraction and detection system of claim 13, wherein the dampeners are active dampeners.

15. The standalone gas extraction and detection system of claim 13, wherein the dampeners are passive dampeners.

16. A method for extracting and detecting a gas, the method comprising:
    extracting the gas from a wellbore fluid that is disposed within an extraction chamber of a standalone gas extraction and detection system;
    allowing extracted gas to move into a detection chamber that is integrated into the extraction chamber of the standalone gas extraction and detection system;
    moving a shaft that extends through the extraction chamber and the detection chamber to extract the gas from the wellbore fluid; and
    detecting infrared radiation via an open-path detector to analyze the extracted gas that is disposed within the detection chamber.

17. The method of claim 16, further comprising mixing the extracted gas with a carrier fluid for passage into the detection chamber.

18. The method of claim 16, further comprising vibrationally isolating the gas detection chamber from other components of the standalone gas extraction and detection system with active dampeners.

19. The method of claim 16, further comprising vibrationally isolating the gas detection chamber from other components of the standalone gas extraction and detection system with passive dampeners.

* * * * *